United States Patent
Lee et al.

(10) Patent No.: US 10,916,724 B2
(45) Date of Patent: Feb. 9, 2021

(54) ORGANIC LIGHT EMITTING DEVICE

(71) Applicant: LG Chem, Ltd., Seoul (KR)

(72) Inventors: Hyungjin Lee, Daejeon (KR); Dongheon Kim, Daejeon (KR); Nansra Heo, Daejeon (KR); Dong Hoon Lee, Daejeon (KR); Wonjoon Heo, Daejeon (KR); Min Woo Jung, Daejeon (KR)

(73) Assignee: LG Chem, Ltd.

( * ) Notice: Subject to any disclaimer, the term of this patent is extended or adjusted under 35 U.S.C. 154(b) by 90 days.

(21) Appl. No.: 15/562,716

(22) PCT Filed: Mar. 17, 2017

(86) PCT No.: PCT/KR2017/002912
§ 371 (c)(1),
(2) Date: Sep. 28, 2017

(87) PCT Pub. No.: WO2017/164574
PCT Pub. Date: Sep. 28, 2017

(65) Prior Publication Data
US 2018/0123069 A1    May 3, 2018

(30) Foreign Application Priority Data

Mar. 21, 2016  (KR) .................. 10-2016-0033512

(51) Int. Cl.
| | |
|---|---|
| H01L 51/50 | (2006.01) |
| H05B 33/12 | (2006.01) |
| H01L 51/00 | (2006.01) |
| C07D 251/24 | (2006.01) |
| C07D 403/10 | (2006.01) |

(52) U.S. Cl.
CPC ........ *H01L 51/5072* (2013.01); *C07D 251/24* (2013.01); *C07D 403/10* (2013.01); *H01L 51/0056* (2013.01); *H01L 51/50* (2013.01); *H05B 33/12* (2013.01); *H01L 51/0052* (2013.01); *H01L 51/0058* (2013.01); *H01L 51/0067* (2013.01); *H01L 51/0072* (2013.01); *H01L 2251/552* (2013.01)

(58) Field of Classification Search
CPC .................................. H01L 2251/552
See application file for complete search history.

(56) References Cited

U.S. PATENT DOCUMENTS

| | | |
|---|---|---|
| 2007/0024188 A1 | 2/2007 | Kim et al. |
| 2008/0241589 A1 | 10/2008 | Fukunaga et al. |
| 2009/0009101 A1 | 1/2009 | Kang et al. |
| 2009/0179559 A1 | 7/2009 | Yoon et al. |

(Continued)

FOREIGN PATENT DOCUMENTS

| | | |
|---|---|---|
| CN | 101960637 A | 1/2011 |
| CN | 104272488 A | 1/2015 |

(Continued)

OTHER PUBLICATIONS

Search report from International Application No. PCT/KR2017/002912, dated Jun. 20, 2017.

(Continued)

*Primary Examiner* — Kenneth Parker
*Assistant Examiner* — Christopher A Culbert
(74) *Attorney, Agent, or Firm* — Lerner, David, Littenberg, Krumholz & Mentlik, LLP

(57) ABSTRACT

The present specification relates to an organic light emitting device.

6 Claims, 1 Drawing Sheet

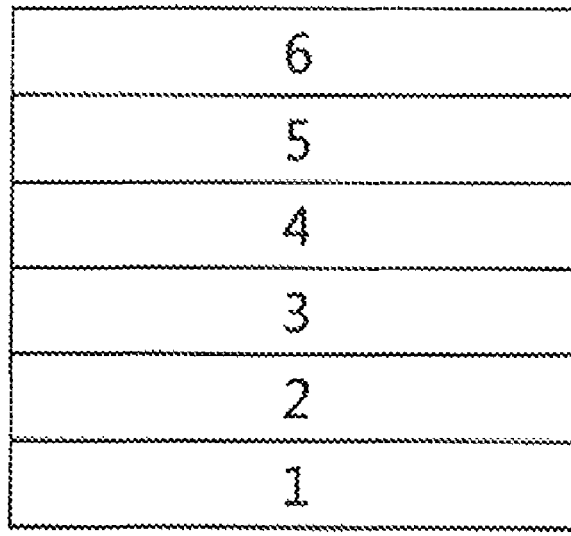

(56) References Cited

U.S. PATENT DOCUMENTS

| | | | |
|---|---|---|---|
| 2011/0037062 A1 | 2/2011 | Fukumatsu et al. | |
| 2011/0147716 A1 | 6/2011 | Kondakova et al. | |
| 2012/0126690 A1* | 5/2012 | Ise | C09K 11/06 313/504 |
| 2013/0248830 A1 | 9/2013 | Welsh et al. | |
| 2015/0144897 A1 | 5/2015 | Kang et al. | |
| 2016/0197282 A1* | 7/2016 | Tanimoto | H01L 51/0057 257/40 |
| 2016/0276594 A1* | 9/2016 | Huh | H01L 51/50 |
| 2016/0365527 A1* | 12/2016 | Gao | C09K 11/025 |
| 2017/0133605 A1* | 5/2017 | Islam | C07D 333/50 |

FOREIGN PATENT DOCUMENTS

| | | |
|---|---|---|
| EP | 1724323 A1 | 11/2006 |
| EP | 2731115 A1 | 5/2014 |
| JP | 2008270736 A | 11/2008 |
| JP | 2009021336 A | 1/2009 |
| JP | 2011091366 A | 5/2011 |
| KR | 20070076521 A | 7/2007 |
| KR | 100894627 B1 | 4/2009 |
| KR | 20120078294 A | 7/2012 |
| KR | 20150075674 A | 7/2015 |
| KR | 101560102 B1 | 10/2015 |
| WO | 2015022988 A1 | 2/2015 |

OTHER PUBLICATIONS

Chinese Search Report for Application No. 2017800011440, dated Sep. 6, 2018.

Extended European Search Report including Written Opinion for Application No. EP17765060.3, dated Oct. 10, 2019, pp. 1-7.

* cited by examiner

| 6 |
|---|
| 5 |
| 4 |
| 3 |
| 2 |
| 1 |

ORGANIC LIGHT EMITTING DEVICE

CROSS-REFERENCE TO RELATED APPLICATION

This application is a national phase entry under 35 U.S.C. § 371 of International Application No. PCT/KR2017/002912, filed Mar. 17, 2017, which claims priority to Korean Patent Application No. 10-2016-0033512, filed Mar. 21, 2016, the disclosures of which are incorporated herein by reference.

TECHNICAL FIELD

The present specification relates to an organic light emitting device.

BACKGROUND ART

An organic light emission phenomenon is one of the examples of converting current into visible rays through an internal process of a specific organic molecule. The principle of the organic light emission phenomenon is as follows. When an organic material layer is disposed between a positive electrode and a negative electrode, if voltage is applied between internal parts of a specific organic molecule through the two electrodes, electrons and holes are injected into the organic material layer from the negative electrode and the positive electrode, respectively. The electrons and the holes which are injected into the organic material layer are recombined to form an exciton, and the exciton falls down again to the ground state to emit light. An organic light emitting device using this principle may generally include an anode, a cathode, and an organic material layer disposed therebetween, for example, an organic material layer including a hole injection layer, a hole transporting layer, a light emitting layer, and an electron transporting layer.

An organic light emitting device means a self-emitting type device using an electroluminescence phenomenon which emits light when current flows through a luminescent organic compound, and has received attention as a next-generation material in various industrial fields such as display and lighting.

There is a need for developing a technology for increasing light emitting efficiency of an organic light emitting device by lowering a driving voltage of the organic light emitting device.

CITATION LIST

Patent Document

Korean Patent Application Laid-Open No. 2007-0076521

DETAILED DESCRIPTION OF THE INVENTION

Technical Problem

The present specification provides an organic light emitting device.

Technical Solution

An exemplary embodiment of the present specification provides an organic light emitting device including: an anode; a cathode provided to face the anode; a light emitting layer provided between the anode and the cathode; and an electron transporting layer provided between the cathode and the light emitting layer, wherein the electron transporting layer comprises a first electron transporting layer and a second electron transporting layer, the first electron transporting layer is provided to be brought into contact with the light emitting layer, and a reorganization energy of the first electron transporting layer is equal to or less than a difference in LUMO energies between the light emitting layer and the first electron transporting layer.

Further, an exemplary embodiment of the present specification provides a display device including the above-described organic light emitting device.

An exemplary embodiment of the present specification provides a lighting device including the organic light emitting device.

Advantageous Effects

The organic light emitting device according to an exemplary embodiment of the present specification may implement low voltage and high efficiency of the organic light emitting device by lowering the degree to which the polaron binding energy contributes to a barrier when electrons move from a first electron transporting layer to a light emitting layer.

BRIEF DESCRIPTION OF DRAWINGS

The Figure illustrates an example of a lamination structure of an organic light emitting device according to an exemplary embodiment of the present specification.

BEST MODE

Hereinafter, the present specification will be described in more detail.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

An exemplary embodiment of the present specification provides an organic light emitting device including: an anode; a cathode provided to face the anode; a light emitting layer provided between the anode and the cathode; and an electron transporting layer provided between the cathode and the light emitting layer, wherein the electron transporting layer comprises a first electron transporting layer and a second electron transporting layer, the first electron transporting layer is provided to be brought into contact with the light emitting layer, and a reorganization energy of the first electron transporting layer is equal to or less than a difference in LUMO energies between the light emitting layer and the first electron transporting layer.

When the reorganization energy of the first electron transporting layer is equal to or less than a difference in LUMO energies between the light emitting layer and the first electron transporting layer, an additional barrier, which electrons feel, evades an effect imposed by the polaron binding energy in the first electron transporting layer by the difference in LUMO energies, thereby implementing the low voltage and high efficiency of the organic light emitting device.

In the present specification, the reorganization energy means a stabilized energy of electrons due to the polaron binding energy ($E_{pol}$=lambda/2), and as the energy of electrons is stabilized, a barrier which electrons feel when moving to an adjacent layer may be increased.

In the present specification, the reorganization energy means a reorganization energy of electrons.

The reorganization energy of electrons in the present specification may be obtained by the following Equation 1.

$$\lambda = \{E_{anion}^{X-} - E_{anion}^{X}\} + \{E_{neutral}^{X-} - E_{neutral}^{X}\} \quad \text{[Equation 1]}$$

In Equation 1,

λ is a reorganization energy, and $E_{geometry}^{charge}$ means an energy in which a charge is X or X⁻ in a structure where geometry is optimized with an anion or a neutral charge.

In the present specification, the optimization of a molecular structure and the calculation of each energy in the calculation of the reorganization energy were obtained by means of a density functional theory (DFT) using a BPW91 functional and a dnd basis function by using Dmol3 which is a quantum chemical calculation program manufactured by Accelrys Software Inc.

According to an exemplary embodiment of the present specification, the reorganization energy of the first electron transporting layer with respect to the difference in LUMO energies between the light emitting layer and the first electron transporting layer is more than 0 and 1 or less. In this case, the low voltage and high efficiency of the organic light emitting device may be implemented by lowering the degree to which the polaron binding energy contributes to a barrier when electrons move from a first electron transporting layer to a light emitting layer.

For example, when the difference in LUMO energies between the light emitting layer and the first electron transporting layer is 0.1 eV, the reorganization energy of the first electron transporting layer is 0.1 eV or less.

In the present specification, a LUMO energy level may be measured by using cyclic voltammetry (CV), which is an electrochemical method, and spectroscopic methods (UV-Vis spectroscopy and photoelectron spectroscopy (PS)).

According to an exemplary embodiment of the present specification, the second electron transporting layer is provided to be brought into contact with the first electron transporting layer.

Further, according to an exemplary embodiment of the present specification, an electron injection layer provided between the cathode and the second electron transporting layer is included.

In addition, according to an exemplary embodiment of the present specification, a LUMO energy value of the second electron transporting layer is 2 eV to 5 eV. When the LUMO energy value of the second electron transporting layer satisfies the range, there is an advantage in that the mobility of electrons which are electron injected from the electron injection layer is excellent by lowering the barrier energy in which electrons injected from the electron injection layer move to the second electron transporting layer.

According to an exemplary embodiment of the present specification, the first electron transporting layer includes any one or more of the following compounds, but is not limited thereto.

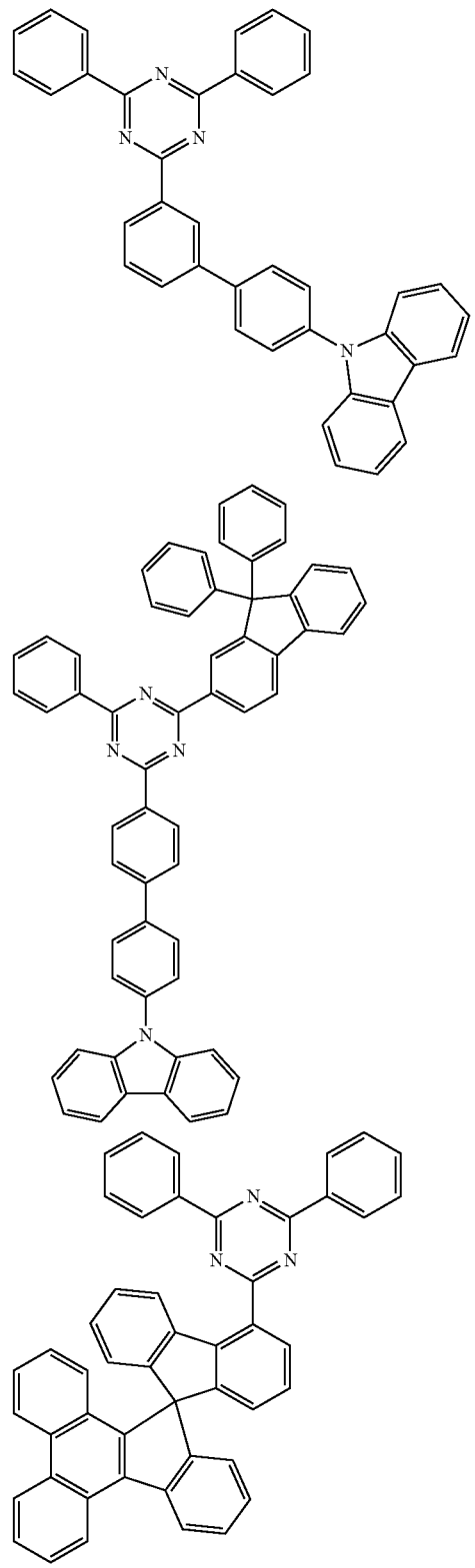

According to an exemplary embodiment of the present specification, a material known in the art may be used as long as a material used as a material for the second electron transporting layer is a material having a LUMO energy value within a range of 2 eV to 5 eV.

According to an exemplary embodiment of the present specification, the first electron transporting layer has a thickness of 5 nm to 10 nm. When the thickness of the first electron transporting layer satisfies the range, the low voltage and high efficiency of the organic light emitting device may be implemented by facilitating the charge movement in the first electron transporting layer.

According to an exemplary embodiment of the present specification, the organic light emitting device may further include one or more selected from the group consisting of a hole injection layer, a hole transporting layer, and an electron blocking layer.

The organic light emitting device of the present specification includes an electron transporting layer provided between the cathode and the light emitting layer, the electron transporting layer includes a first electron transporting layer and a second electron transporting layer, and the organic light emitting device may be manufactured by using materials and methods known in the art, except that the reorganization energy of the first electron transporting layer is equal to or less than a difference in LUMO energies between the light emitting layer and the first electron transporting layer.

For example, the organic light emitting device of the present specification may be manufactured by sequentially stacking an anode, a light emitting layer, a first electron transporting layer, a second electron transporting layer, and a cathode on a substrate. In this case, the organic light emitting device may be manufactured by depositing a metal or a metal oxide having conductivity, or an alloy thereof on a substrate to form an anode, forming a hole injection layer, a hole transporting layer, an electron blocking layer, a light emitting layer, a first electron transporting layer, a second electron transporting layer, and an electron injection layer thereon, and then depositing a material, which may be used as a cathode, thereon, by using a physical vapor deposition (PVD) method such as sputtering or e-beam evaporation. In addition to the method described above, an organic light emitting device may be made by sequentially depositing a cathode material, an electron injection layer, a second electron transporting layer, a first electron transporting layer, a light emitting layer, an electron blocking layer, a hole transporting layer, a hole injection layer, and an anode material on a substrate.

For example, the structure of the organic light emitting device of the present specification may have a structure as illustrated in the Figure, but is not limited thereto.

The Figure exemplifies the structure of an organic light emitting device in which an anode 2, a light emitting layer 3, a first electron transporting layer 4, a second electron transporting layer 5, and a cathode 6 are sequentially stacked on a substrate 1. In the Figure, a reorganization energy of the first electron transporting layer is equal to or less than a difference in LUMO energies between the light emitting layer and the first electron transporting layer.

The Figure is an exemplified structure of the organic light emitting device according to an exemplary embodiment of the present specification, and may further include one or more selected from the group consisting of a hole injection layer, a hole transporting layer, and an electron blocking layer.

The substrate may be a glass substrate or a transparent plastic substrate having excellent transparency, surface smoothness, ease of handling, and waterproofing properties, but is not limited thereto, and the substrate is not limited as long as the substrate is typically used in the organic light emitting device.

As the anode material, materials having a high work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene](PEDOT), polypyrrole, and polyaniline; and the like, but are not limited thereto.

As the cathode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The light emitting material is a material which may emit light in a visible light region by accepting and combining holes and electrons from a hole transporting layer and an electron transporting layer, respectively, and is preferably a material having high quantum efficiency for fluorescence or phosphorescence. Specific examples thereof include: an 8-hydroxy-quinoline aluminum complex (Alq$_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the materials to be used.

According to an exemplary embodiment of the present specification, the organic light emitting device may be a flexible organic light emitting device. In this case, the substrate may include a flexible material. Specifically, the substrate may be a glass in the form of a thin film which may be bent, a plastic substrate, or a substrate in the form of a film.

A material for the plastic substrate is not particularly limited, but may be generally a material including a film such as PET, PEN, PEEK, and PI in the form of a single layer or multiple layers.

The present specification provides a display device including the organic light emitting device. The organic light emitting device in the display device may serve as a pixel or a backlight. In addition, as a configuration of the display device, those known in the art may be applied.

The present specification provides a lighting device including the organic light emitting device. In the lighting device, the organic light emitting device serves as a light emitting unit. In addition, as the configurations required for the lighting device, those known in the art may be applied.

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

Example 1

A glass substrate (Corning 7059 glass) on which a thin film of indium tin oxide (ITO) was coated to have a thickness of 1,300 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. In addition, the substrate was dry washed using oxygen plasma for 5 minutes, and then was transported to a vacuum deposition machine.

The compound of the following Chemical Formula hexanitrilehexaazatriphenylene (hereinafter, referred to as HAT) was thermally vacuum deposited to a thickness of 50 Å on the ITO transparent electrode, which was prepared as described above, thereby forming a thin film. Interfacial characteristics between the substrate and a hole injection layer may be improved by the thin film. Subsequently, a compound of the following Chemical Formula HT-1 was deposited to have a thickness of 1,200 Å on the thin film, thereby forming a hole transporting layer, and the following H1 (2-methyl-9,10-di(2-naphthyl)anthracene (MADN)) and a compound of the following D1 were vacuum deposited as a host and a dopant of a light emitting layer, respectively, to have a thickness of 200 Å thereon. A first electron transporting layer was vacuum deposited to have a thickness of 100 Å on the light emitting layer by using the following Compound 1. A second electron transporting layer was vacuum deposited to have a thickness of 200 Å on the first electron transporting layer by using a compound ET 1. Lithium fluoride (LiF) and aluminum were subsequently deposited to have a thickness of 10 Å and 1,000 Å, respectively, on the electron transporting layer, thereby forming a negative electrode.

In the aforementioned procedure, the deposition rate of the organic material was maintained at 0.3 to 0.8 Å/sec. Furthermore, the deposition rates of lithium fluoride and aluminum in the negative electrode were maintained at 0.3 Å/sec and at 1.5 to 2.5 Å/sec, respectively. The degree of vacuum during the deposition was maintained at 1 to $3 \times 10^{-7}$ torr.

[HAT]

[H1]

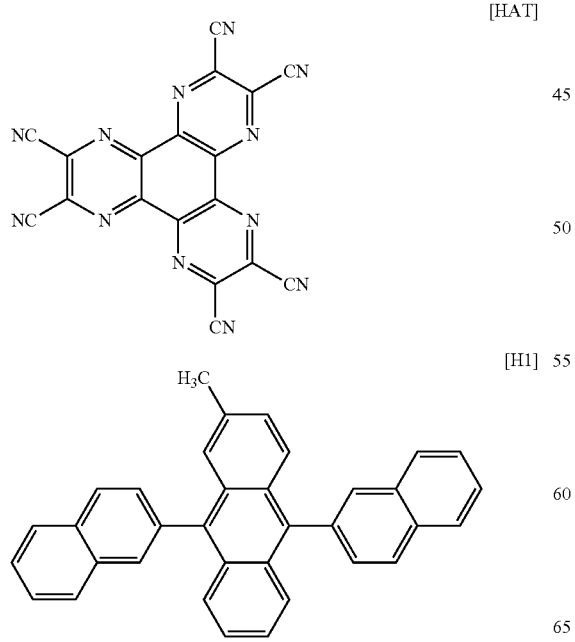

[D1]

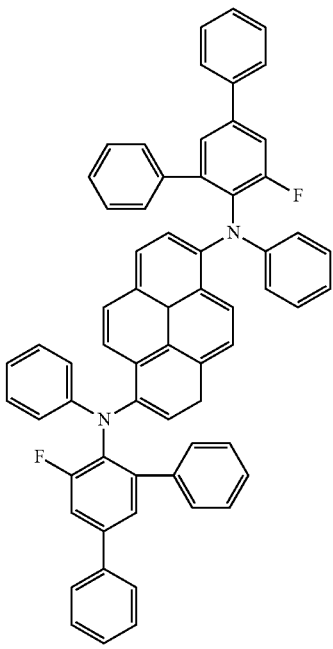

[HT-1]

[Compound 1]

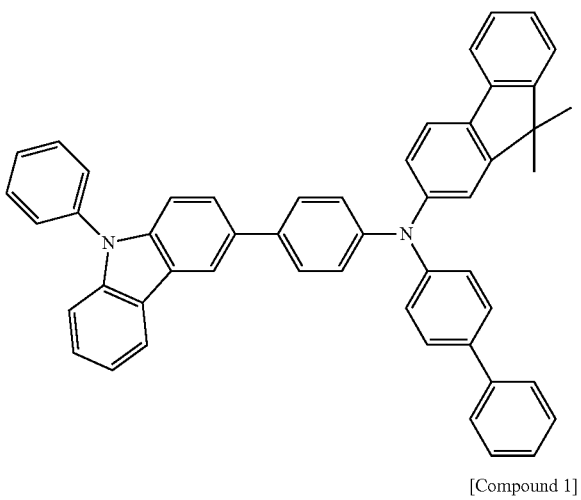

-continued

[ET1]

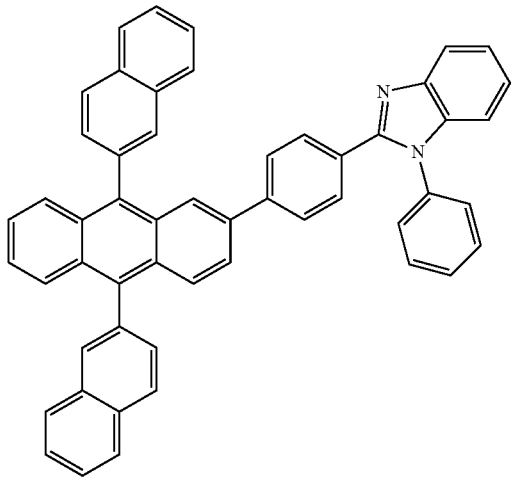

Example 2

An experiment was performed in the same manner as in Example 1, except that as the first electron transporting layer, the following Compound 2 was used instead of Compound 1 in Example 1.

[Compound 2]

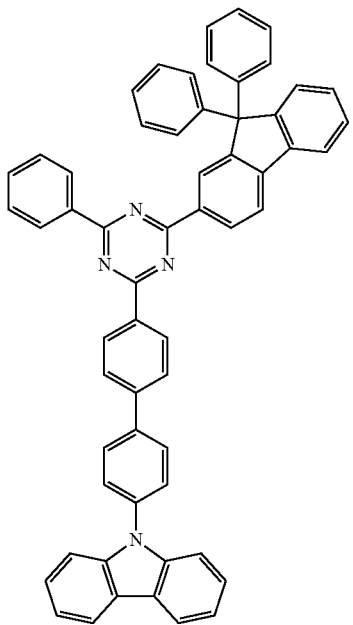

Example 3

An experiment was performed in the same manner as in Example 1, except that as the first electron transporting layer, the following Compound 3 was used instead of Compound 1 in Example 1.

[Compound 3]

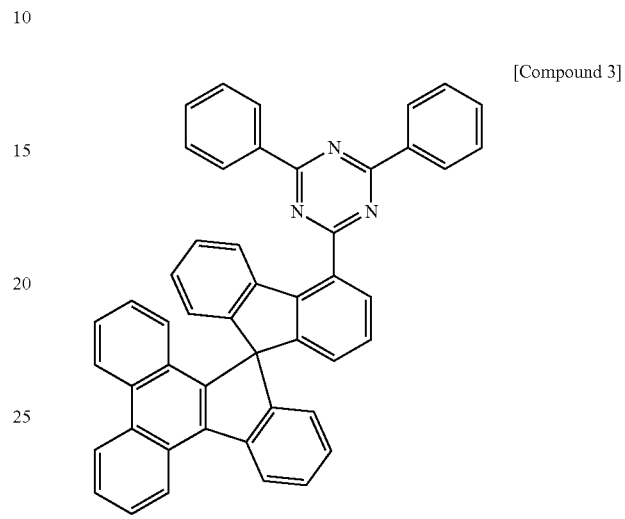

Comparative Example 1

An experiment was performed in the same manner as in Example 1, except that as the first electron transporting layer, the following Compound A was used instead of Compound 1 in Example 1.

[Compound A]

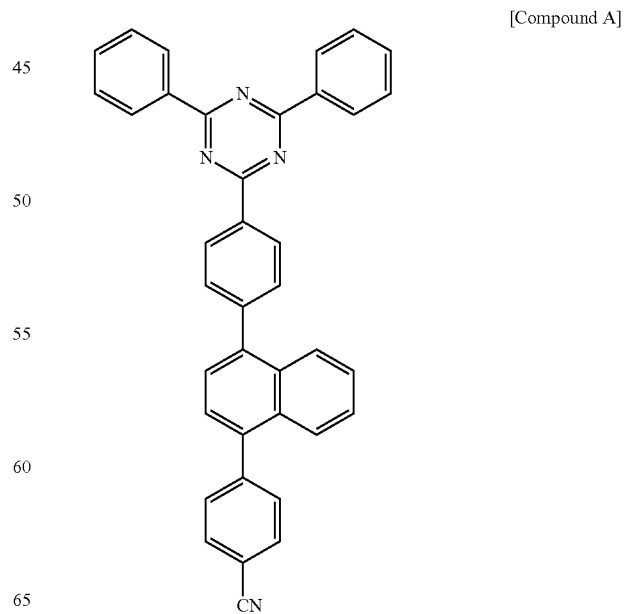

Comparative Example 2

An experiment was performed in the same manner as in Example 1, except that as the first electron transporting layer, the following Compound B was used instead of Compound 1 in Example 1.

Comparative Example 3

An experiment was performed in the same manner as in Example 1, except that as the first electron transporting layer, the following Compound C was used instead of Compound 1 in Example 1.

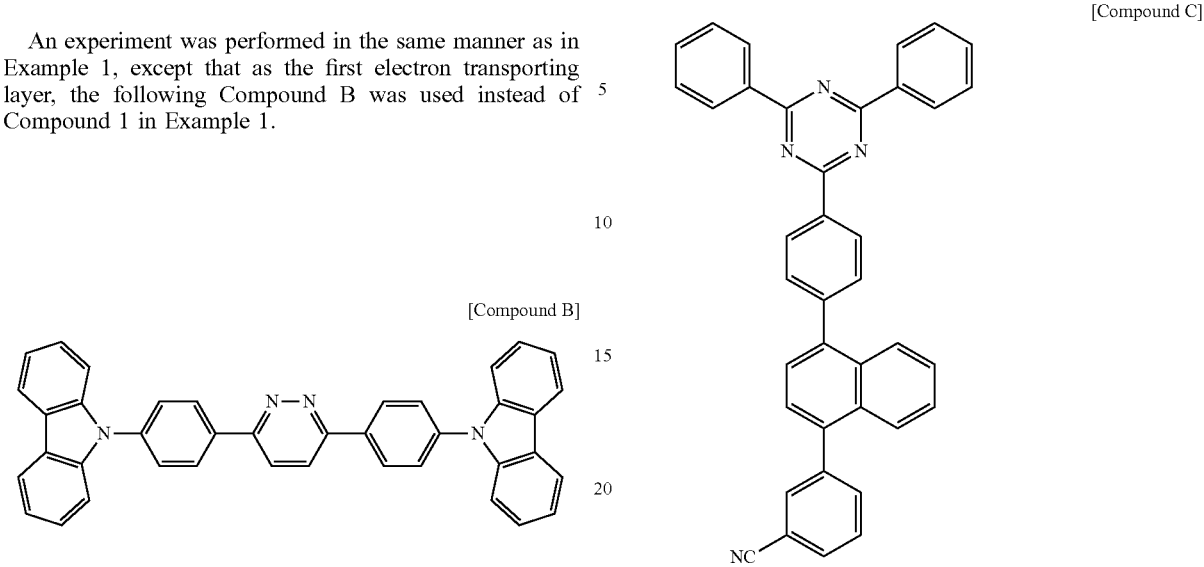

[Compound B]

[Compound C]

The physical properties of the compounds used for the first electron transporting layers of the organic light emitting devices manufactured by Examples 1 to 3 and Comparative Examples 1 to 3 are shown in Table 1, and for the organic light emitting devices manufactured by Examples 1 to 3 and Comparative Examples 1 to 3, the driving voltages and light emitting efficiencies were measured at a current density of 10 mA/cm², and time ($T_{95}$) taken for the luminance to become 95% as compared to the initial luminance was measured at a current density of 20 mA/cm². The results are shown in the following Table 2.

TABLE 1

|  | Compound | HOMO (eV) | LUMO (eV) | Gap (eV) | Reorganization energy of first electron transporting layer (eV) | Difference in LUMO energies between light emitting layer and first electron transporting layer (eV) | Reorganization energy of first electron transporting layer/Difference in LUMO energies between light emitting layer and first electron transporting layer |
|---|---|---|---|---|---|---|---|
| Example 1 | Compound 1 | 5.85 | 2.75 | 3.1 | 0.14 | 0.25 | 0.56 |
| Example 2 | Compound 2 | 5.79 | 2.78 | 3.02 | 0.18 | 0.28 | 0.64 |
| Example 3 | Compound 3 | 5.87 | 2.78 | 3.09 | 0.11 | 0.28 | 0.39 |
| Comparative Example 1 | Compound A | 6.14 | 2.76 | 3.38 | 0.31 | 0.26 | 1.19 |
| Comparative Example 2 | Compound B | 5.81 | 2.79 | 3.02 | 0.33 | 0.29 | 1.14 |
| Comparative Example 3 | Compound C | 6.13 | 2.71 | 3.42 | 0.27 | 0.21 | 1.29 |

TABLE 2

|  | Compound | Voltage (V@10 mA/cm²) | Efficiency (cd/A@10 mA/cm²) | Luminous flux efficiency (Lm/W) | η (QE) | Color coordinate (x, y) | Service life (h) $T_{95}$ at 20 mA/cm² |
|---|---|---|---|---|---|---|---|
| Example 1 | Compound 1 | 4.07 | 5.90 | 4.55 | 6.36 | (0.312, 0.120) | 90 |
| Example 2 | Compound 2 | 4.32 | 5.74 | 4.18 | 5.84 | (0.132, 0.134) | 112 |

TABLE 2-continued

|  | Compound | Voltage (V@10 mA/cm$^2$) | Efficiency (cd/A@10 mA/cm$^2$) | Luminous flux efficiency (Lm/W) | η (QE) | Color coordinate (x, y) | Service life (h) T$_{95}$ at 20 mA/cm$^2$ |
|---|---|---|---|---|---|---|---|
| Example 3 | Compound 3 | 4.16 | 5.79 | 4.37 | 6.24 | (0.132, 0.124) | 94 |
| Comparative Example 1 | Compound A | 4.67 | 5.58 | 3.08 | 4.66 | (0.132, 0.133) | 85 |
| Comparative Example 2 | Compound B | 4.41 | 5.16 | 3.68 | 5.38 | (0.131, 0.129) | 74 |
| Comparative Example 3 | Compound C | 4.50 | 5.08 | 3.55 | 5.47 | (0.132, 0.121) | 67 |

As in Table 1, it can be seen that the reorganization energy of each of the first electron transporting layers in Examples 1 to 3 is equal to or less than a difference in LUMO energies between the light emitting layer and the first electron transporting layer, but the reorganization energy of each of the first electron transporting layers in Comparative Examples 1 to 3 is larger than the difference in LUMO energies between the light emitting layer and the first electron transporting layer. Further, it can be seen that for the difference in LUMO energies between the light emitting layer and the first electron transporting layer in Examples 1 to 3, the reorganization energy of the first electron transporting layer is 1 or less. In Table 2 which compares the organic light emitting devices in Examples 1 to 3 manufactured by using Compounds 1 to 3 having the reorganization energy and the organic light emitting devices in Comparative Examples 1 to 3, it could be seen that the organic light emitting devices in Examples 1 to 3 had lower voltage and better efficiency and service life than the organic light emitting devices in Comparative Examples 1 to 3.

In Table 2, η means quantum efficiency according to the current density.

EXPLANATION OF REFERENCE NUMERALS AND SYMBOLS

1: Substrate
2: Anode
3: Light emitting layer
4: First electron transporting layer
5: Second electron transporting layer
6: Cathode

The invention claimed is:
1. An organic light emitting device comprising:
an anode;
a cathode provided to face the anode;
a light emitting layer provided between the anode and the cathode; and
an electron transporting layer provided between the cathode and the light emitting layer,
wherein the electron transporting layer comprises a first electron transporting layer and a second electron transporting layer,
the first electron transporting layer is provided to be brought into contact with the light emitting layer,
the light emitting layer comprises a host material and a dopant material, and the host material is an anthracene derivative, and the dopant material is a pyrene derivative which has an arylamino group,
wherein the reorganization energy of the first electron transporting layer with respect to the difference in LUMO energies between the light emitting layer and the first electron transporting layer is more than 0.39 and 0.64 or less,
the first electron transporting layer comprises at least one of the following compounds:

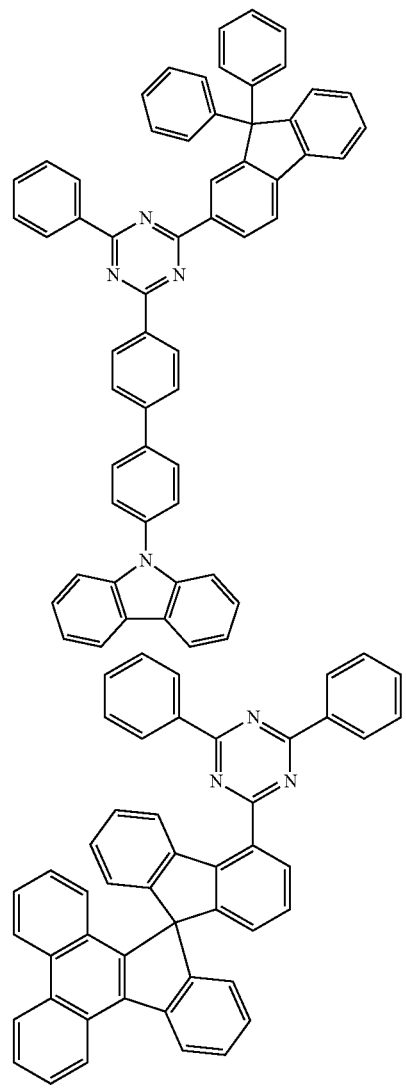

and the second electron transporting layer comprises the following compound:

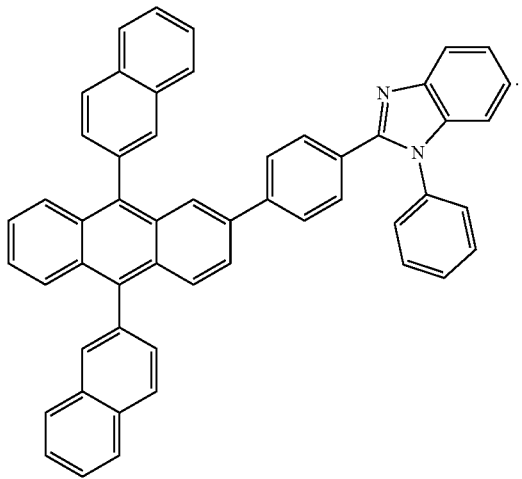 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

2. The organic light emitting device of claim 1, wherein the second electron transporting layer is provided to be brought into contact with the first electron transporting layer.

3. The organic light emitting device of claim 1, wherein a LUMO energy value of the second electron transporting layer is 2 eV to 5 eV.

4. The organic light emitting device of claim 1, wherein the first electron transporting layer has a thickness of 5 nm to 10 nm.

5. A display device comprising the organic light emitting device of claim 1.

6. A lighting device comprising the organic light emitting device of claim 1.

* * * * *